United States Patent [19] [11] 4,418,228
Harrison et al. [45] Nov. 29, 1983

[54] PROCESS FOR RING BROMINATION OF NITROBENZENE

[75] Inventors: James J. Harrison, Glenshaw; John P. Pellegrini, Pittsburgh; Charles M. Selwitz, Monroeville, all of Pa.

[73] Assignee: Gulf Research & Development Company, Pittsburgh, Pa.

[21] Appl. No.: 370,733

[22] Filed: Apr. 22, 1982

[51] Int. Cl.³ .............................................. C07C 79/12
[52] U.S. Cl. .................................................. 568/937
[58] Field of Search ............................... 568/937, 938

[56] References Cited

U.S. PATENT DOCUMENTS 2,387,341 10/1945 Ogilvie et al. ...................... 568/937
2,429,493 10/1947 Sievenpiper et al. ............... 568/937

Primary Examiner—Leland A. Sebastian
Attorney, Agent, or Firm—Deane E. Keith; Forrest D. Stine; Joseph J. Carducci

[57] ABSTRACT

A process for ring bromination of nitrobenzene which comprises contacting the nitrobenzene with an alkali metal bromate and aqueous sulfuric acid.

6 Claims, No Drawings

PROCESS FOR RING BROMINATION OF NITROBENZENE

BACKGROUND OF THE INVENTION

1. Field of the Invention

This invention relates to a process for ring bromination of nitrobenzene which comprises contacting nitrobenzene with an alkali metal bromate and aqueous sulfuric acid wherein the weight percent sulfuric acid is in the range of about 52 to about 75 percent.

2. Description of the Prior Art

J. R. Johnson et al., Org. Syn., John Wiley, New York, N.Y., Collect., Vol. 1, 1956, page 123, state that nitrobenzene can be brominated using bromine and iron powder at temperatures of 135° to 145° C. A 65 to 75 percent yield was reported.

In C.A. 55:8348 d it is reported that B. V. Tronov et al. [Izvest. Vyssh. Ucheb Zaredenii i Khin i Khin Technology 3 872 (1960)] obtained 33 percent yield of bromonitrobenzene by brominating nitrobenzene using bromine, sulfuric acid, nitric acid and acetic acid over a period of 4.5 hours at 83° C.

In C.A. 49:13133 f it is reported that B. V. Tronov et al. [Zhur. Obschehei, Khin. 24 1608 (1954)] reacted nitrobenzene with bromine using aluminum, sulfur and tellurium as catalysts.

K. Huthmacher et al., Synthesis (1978) 693 report that a mixture of potassium-peroxydisulfate and bromine produces a 30 percent yield of bromonitrobenzene using five percent fuming sulfuric acid at room temperature. In addition, they use the reagent $AgO-SO_2-CF_3$ at room temperature and over a period of four to 16 hours to obtain 74 and 83 percent bromonitrobenzene.

D. H. Derbyshere et al., J. Chem. Soc. 573 (1950), report that nitrobenzene can be brominated by reacting nitrobenzene with bromine water and silver sulfate. The HOBr was prepared in situ. The reaction was carried over a period of 16 hours at room temperature.

F. L. Lambert et al., J. Org. Chem. (1965) 30, 304, report brominating nitrobenzene using 50 percent sulfuric acid by volume and n-bromo succinimide over a period of three hours at 85°-90° C. to obtain a yield of 70 percent.

W. Gottardi, Monatsch Chem., 99, 815 (1968) obtain a yield of 88 percent bromonitrobenzene over a period of five minutes at 20° C. using dibromoisocyanuric acid in concentrated sulfuric acid (96 percent).

SUMMARY OF THE INVENTION

We have found that we can obtain ring bromination of nitrobenzene by contacting the same with an alkali metal bromate and aqueous sulfuric acid wherein the weight percent sulfuric acid in the reaction solution (concentration) is in the critical range of about 52 to about 75 percent, preferably about 55 to about 72 percent.

Among the alkali metal bromates that can be used herein, mention can be made of sodium bromate and potassium bromate.

In carrying out the bromination process defined and claimed herein, the components required, namely, the nitrobenzene, the alkali metal bromate and the aqueous sulfuric acid having a weight concentration of about 52 to about 75 weight percent, preferably about 55 to about 72 weight percent, can be brought together in any convenient or suitable manner. In a preferred procedure the nitrobenzene is added to the aqueous sulfuric acid. The alkali metal bromate is then added last, since it is thus easier to control the temperature of reaction.

The amounts of each of the components, and particularly the concentration of the sulfuric acid, are critical in order to obtain optimum yields of brominated nitrobenzene. Based on the total reaction mixture, the concentration of the nitrobenzene will be in the range of about 0.25 to about 2.0 mols per liter of solution, preferably about 0.75 to about 1.75 mols per liter of solution, and the amount of alkali metal bromate will be in the range of about 0.25 to about 2.5 mols per liter of solution, preferably about 0.75 to about 2.0 mols per liter of solution. The amount of sulfuric acid will be such that its concentration in the reaction solution will be in the range of about 52 to about 75 weight percent, preferably about 55 to about 72 weight percent.

The reactor components defined above, after being brought together, are mixed for about 10 minutes to about 24 hours, or even longer, preferably about one to about four hours, while maintaining a temperature of about −10° to about 100° C., preferably about 0° to about 60° C. Pressure is not important and therefore atmospheric, or ambient, pressure is preferred. At the end of the reaction period, the reaction product is filtered. The solid product recovered is washed with an equal volume of water and dried.

DESCRIPTION OF PREFERRED EMBODIMENTS

A number of runs was carried out exemplifying the process defined and claimed herein.

EXAMPLE I

In each of several runs, to a glass beaker equipped with a mechanical stirrer, thermometer, watercooling coil and cooling bath, there were added aqueous sulfuric acid, water and nitrobenzene. In each case the contents were cooled to 25° C. and solid potassium bromate was added in portions while maintaining the temperature between 25° and 35° C. by the rate of addition and by adjusting the cooling bath. After the addition was complete, the reaction was stirred while maintaining a reaction temperature in the range of 30° to 60° C. for a period of one to 24 hours and then filtered. The pale yellow solids obtained were then washed twice with an equal volume of water and dried under suction overnight. The product resulting from the above was then identified as 3-bromonitrobenzene by gas chromatography. The results of a series of runs carried out following the above procedure are set forth below in Table I.

TABLE I

| Run No. | KBrO$_3$ Grams, (Mol/Liter) | Nitrobenzene, Grams (Mol/Liter) | Water, Grams | Sulfuric Acid, g. | Sulfuric Acid Concentration, Wt % | Temp., °C. | Reaction Time, Hrs. | % Yield of 3-bromo-nitrobenzene |
|---|---|---|---|---|---|---|---|---|
| 1 | 1.67 (1.05) | 1.23 (1.05) | 9.0 | 1.0 | 10 | 30 | 24 | 0 |
| 2 | 1.67 (1.10) | 1.23 (1.10) | 8.0 | 2.0 | 20 | 30 | 24 | 0 |

TABLE I-continued

| Run No. | KBrO$_3$ Grams, (Mol/Liter) | | Nitrobenzene, Grams (Mol/Liter) | | Water, Grams | Sulfuric Acid, g. | Sulfuric Acid Concentration, Wt % | Temp., °C. | Reaction Time, Hrs. | % Yield of 3-bromo-nitrobenzene |
|---|---|---|---|---|---|---|---|---|---|---|
| 3 | 1.67 | (1.16) | 1.23 | (1.16) | 7.0 | 3.0 | 30 | 30 | 24 | 0 |
| 4 | 1.67 | (1.19) | 1.23 | (1.19) | 6.6 | 3.3 | 33 | 60 | 1 | 0 |
| 5 | 1.67 | (1.22) | 1.23 | (1.22) | 6.0 | 4.0 | 40 | 30 | 24 | Trace |
| 6 | 1.67 | (1.30) | 1.23 | (1.30) | 5.0 | 5.0 | 50 | 30 | 24 | 3 |
| 7 | 1.67 | (1.38) | 1.23 | (1.38) | 4.0 | 6.0 | 60 | 30 | 24 | 73 |
| 8 | 551.0 | (0.70) | 369.0 | (0.64) | 2400 | 4239 | 64 | 35 | 4 | 88 |
| 9 | 551.0 | (0.70) | 369.0 | (0.64) | 2400 | 4239 | 64 | 35 | 4 | 76 |

EXAMPLE II

In each of several additional runs, to an eight-liter beaker equipped with a mechanical stirrer, thermometer, water-cooling coil and cooling bath there was added potassium bromate in water. To this was added nitrobenzene. Then over a period of two hours, concentrated sulfuric acid was added, while maintaining the temperature between 18° and 28° C. After the mixture was stirred for an additional period of time, the product was filtered and washed with one liter of water. The product of the above was then identified as 3-bromonitrobenzene by gas chromatography. The results of a series of runs carried out following the above procedure are set forth below in Table II.

TABLE II

| Run No. | KBrO$_3$ Grams, (Mol/Liter) | | Nitrobenzene, Grams (Mol/Liter) | | Water, Grams | Sulfuric Acid, g. | Sulfuric Acid Concentration, Wt % | Temp., °C. | Reaction Time, Hrs. | % Yield of 3-bromo-nitrobenzene |
|---|---|---|---|---|---|---|---|---|---|---|
| 10 | 501 | (0.64) | 369 | (0.64) | 2400 | 4239 | 64 | 35 | 4 | 80 |
| 11 | 16.7 | (0.68) | 12.3 | (0.68) | 70 | 141 | 67 | 35 | 4 | 73 |
| 12 | 501 | (0.68) | 369 | (0.68) | 2100 | 4239 | 67 | 35 | 4 | 75 |
| 13 | 16.7 | (0.60) | 12.3 | (0.60) | 70 | 177 | 72 | 35 | 2 | 62 |

The results obtained in the above examples are unexpected. Thus, while Y. Furuya et al., Biell. Chem. Soc. Japan, 41, 997 (1968) reported that potassium bromate brominated benzene in acetic acid in the presence of a catalytic amount of sulfuric acid, under the same conditions, they were unable to brominate nitrobenzene. It was surprising, therefore, that by using critical concentrations of sulfuric acid herein described, excellent yields of bromonitrobenzene are obtained.

Obviously, many modifications and variations of the invention, as hereinabove set forth, can be made without departing from the spirit and scope thereof, and therefore only such limitations should be imposed as are indicated in the appended claims.

We claim:

1. A process for ring bromination of nitrobenzene which comprises contacting nitrobenzene with an alkali metal bromate and aqueous sulfuric acid, the reaction mixture being such that the amount of nitrobenzene therein will be in the range of about 0.25 to about 2.0 mols per liter of solution, the amount of alkali metal bromate being in the range of about 0.25 to about 2.5 mols per liter of solution and the concentration of the sulfuric acid in the reaction mixture being in the range of about 52 to about 75 weight percent.

2. The process of claim 1 in which the range of the nitrobenzene is from about 0.75 to about 1.75 mols per liter, the alkali metal bromate is in the range of about 0.75 to about 2.0 mols per liter, and the concentration of the sulfuric acid is in the range of about 55 to about 72 weight percent.

3. The process of claim 1 wherein the alkali metal bromate is potassium bromate.

4. The process of claim 2 wherein the alkali metal bromate is potassium bromate.

5. The process of claim 1 wherein the alkali metal bromate is sodium bromate.

6. The process of claim 2 wherein the alkali metal bromate is sodium bromate.

* * * * *